United States Patent [19]

Steiner et al.

[11] 4,245,098

[45] Jan. 13, 1981

[54] PROCESS FOR PRODUCING 2,3,5-TRICHLOROPYRIDINE, 2,4,4-TRICHLORO-4-FORMYL-BUTYRONITRILE AS A NOVEL COMPOUND AND A PROCESS FOR PRODUCING IT

[75] Inventors: Eginhard Steiner, Füllinsdorf; Pierre Martin, Rheinfelden; Daniel Bellus, Riehen, all of Switzerland

[73] Assignee: Ciba-Geigy Corporation, Ardsley, N.Y.

[21] Appl. No.: 98,017

[22] Filed: Nov. 28, 1979

[30] Foreign Application Priority Data

| Dec. 5, 1978 [CH] | Switzerland | 12394/78 |
| Dec. 5, 1978 [CH] | Switzerland | 12395/78 |
| Oct. 23, 1979 [CH] | Switzerland | 9488/79 |
| Oct. 23, 1979 [CH] | Switzerland | 9489/79 |

[51] Int. Cl.$^3$ .................................................. C07D 213/61
[52] U.S. Cl. .................................. 546/250; 260/465.7
[58] Field of Search .......................... 546/250; 260/465.7

[56] References Cited

FOREIGN PATENT DOCUMENTS

| 2329731 | 1/1974 | Fed. Rep. of Germany. |
| 2709108 | 9/1977 | Fed. Rep. of Germany. |
| 1024399 | 3/1966 | United Kingdom. |
| 1215387 | 12/1970 | United Kingdom. |

OTHER PUBLICATIONS

Sell et al., "J. Chem. Soc.", vol. 73, pp. 432–441, (1898).
Sell et al., "J. Chem. Soc.", vol. 93, pp. 2001–2003, (1908).
Cava et al., "J. Org. Chem.", vol. 23, pp. 1614–1616, (1958).
Koenigs et al., "Ber. Dtsch. Chem. Ges.", vol. 17, pp. 1832–1835, (1884).
Zentralblatt (II), p. 1671, (1928).
O. Fischer, "J. Prak Chem.", [2] vol. 93, p. 371, (1916).
Ruth "Ann. der Chemie", vol. 486, pp. 71–75, (1931).
O. Fischer, "Ber. Dtsch. Chem. Ges.", vol. 31, pp. 609–612, (1898).
O. Fischer, "Ber. Dtsch. Chem. Ges.", vol. 32, pp. 1297–1307, (1899).

*Primary Examiner*—Henry R. Jiles
*Assistant Examiner*—Robert T. Bond
*Attorney, Agent, or Firm*—Frederick H. Rabin

[57] ABSTRACT

A novel process for producing 2,3,5-trichloropyridine is described. The process comprises the addition reaction of trichloroacetaldehyde with acrylonitrile in the presence of a catalyst, and the subsequent cyclization of the intermediately formed 2,4,4-trichloro-4-formyl-butyronitrile, with the splitting-off of water, to give 2,3,5-trichloropyridine.

2,4,4-Trichloro-4-formylbutyronitrile occurring as an intermediate product in the process according to the invention is a novel compound. It can be produced by the addition reaction of trichloroacetaldehyde with acrylonitrile in the presence of a catalyst.

2,3,5-Trichloropyridine can be used as intermediate for the production of herbicidal active substances.

29 Claims, No Drawings

PROCESS FOR PRODUCING 2,3,5-TRICHLOROPYRIDINE, 2,4,4-TRICHLORO-4-FORMYL-BUTYRONITRILE AS A NOVEL COMPOUND AND A PROCESS FOR PRODUCING IT

The present invention relates to a process for producing 2,3,5-trichloropyridine, 2,4,4-trichloro-4-formylbutyronitrile as a novel compound and to a process for producing this compound.

The processes that have hitherto become known for producing 2,3,5-trichloropyridine are unsatisfactory in various respects. 2,3,5-Trichloropyridine can be obtained for example by reacting over several weeks chlorine with pyridine saturated with hydrogen chloride; by prolonged heating of pyridine with phosphorus pentachloride at 210°–220° C.; or by heating an anhydrous barium salt of pyridine-3,5-disulfonic acid with phosphorus pentachloride at about 200° C. There are however formed, in addition to the desired 2,3,5-trichloropyridine, also considerable amounts of other chloropyridines, particularly dichloropyridines and pentachloropyridines (see J. Chem. Soc., 73, 437 (1898), J. Chem. Soc., 93, 2001 (1908) and Ber. Dtsch. Chem. Ges., 17, 1832 (1884).

2,3,5-Trichloropyridine can also be produced by treating 2-amino-3,5-dichloropyridine with potassium nitrite in the presence of a hydrogen halide, especially concentrated hydrochloric acid (see Zentralblatt II, 1671 (1928) and British Pat. No. 1,215,387); or by heating 1-methyl-3,5-dichloropyrid-2-one with phosphorus pentachloride and a small amount of phosphorus oxychloride, or with phosgene, at temperatures between about 150° and 180° C. (see J. pr. Chem. (2), 93, 371 (1916) and Ann. Chem. 486, 71 (1931)). The starting products required for these syntheses are obtainable only by multistage and therefore uneconomical processes (see, for example, J. Org. Chem. 23, 1614 (1958), Ber. Dtsch. Chem. Ges. 31, 609 (1898) and ibid 32, 1297 (1899)). From an ecological standpoint too, these prior known processes are questionable on account of the chlorinating agents and other auxiliary chemicals required in considerable excess. And finally also the yields of 2,3,5-trichloropyridine are in some cases unsatisfactory.

It is known on the other hand from the British Pat. No. 1,024,399 that halogen compounds, such as sulfonyl halides, allyl halides and halogenonitriles, can be caused to undergo an addition reaction, in the presence of catalysts, with ethylenically unsaturated compounds, such as olefins having conjugated double bonds, acrylic acid and acrylic acid derivatives. There are formed in the process exclusively open-chain products.

Finally, there is described in the German Offenlegungsschrift No. 2,709,108 a process for producing 3,5-dichloro-2-hydroxypyridine derivatives. In this process, trichloroacetonitrile is reacted with alkenylaldehydes, for example acrolein, or alkylalkenyl ketones, for example methylvinyl ketone, with the addition of radical initiators. The 2,2,4-trichloropentan-5-one-carboxylic acid nitrile derivatives formed can be cyclised thermally or by the action of Lewis acids, and subsequently converted, by splitting off hydrogen chloride, into a 3,5-dichloro-2-hydroxypyridine derivative.

It has now been found that 2,3,5-trichloropyridine can be produced, in a simple, economical and ecologically favourable manner, in good yields and with use of cheap readily available material, by causing trichloroacetaldehyde to undergo an addition reaction, in the presence of a catalyst, with acrylonitrile; and cyclising the formed 2,4,4-trichloro-4-formylbutyronitrile of the formula I

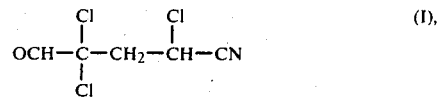

with the splitting off of water, to 2,3,5-trichloropyridine.

The addition reaction of trichloroacetaldehyde with acrylonitrile can be performed, in an open or closed system, at a temperature of 70°–140° C. The addition reaction is preferably performed in a closed system under a pressure corresponding to the applied reaction temperature, which pressure can be for example in the range of 1–30 bars.

As catalysts for the addition reaction of trichloroacetaldehyde with acrylonitrile, there can be used according to the invention metals of the main group VIII and of the subgroups VIa, VIIa, Ib and IIb of the periodic system, for example: iron, cobalt, nickel, ruthenium, rhodium, palladium, chromium, molybdenum, manganese, copper, and zinc. These metals can be used either in elementary form or in the form of compounds. Suitable compounds are for example oxides and salts, such as halides, sulfates, sulfites, sulfides, nitrates, acetates, stearates, citrates, carbonates, cyanides and rhodanides, as well as complexes with ligands, such as phosphines, phosphites, benzoyl- and acetylacetonates, nitriles, isonitriles and carbon monoxide. The following examples may be mentioned: copper(II)oxide, iron(III)oxide; copper(I)-, copper(II)-, iron(II)- and iron(III)bromide, -iodides and in particular -chlorides, zinc chloride, as well as the chlorides of ruthenium, rhodium, palladium, cobalt and nickel; copper(II)sulfate, iron(II)- and iron(III)sulfate; copper(II)nitrate and iron(III)nitrate; manganese(III)acetate, copper(II)acetate, copper(II)stearate, iron(III)citrate, copper(I)cyanide; ruthenium(II)-dichloro-tris-triphenylphosphine, rhodium-dichloro-tris-triphenylphosphine; chromium and nickel acetylacetonate, copper(II)acetylacetonate, iron(III)acetylacetonate, cobalt(II)- and cobalt(III)acetylacetonate, manganese(II)acetonylacetonate, copper(II)benzylacetonate; iron carbonyl-cyclopentadienyl complex; molybdenum carbonylcyclopentadienyl complex, chromium tricarbonylaryl complexes, ruthenium(II)acetato complex, chromium and molybdenum hexacarbonyl, nickel tetracarbonyl, iron pentacarbonyl, cobalt and manganese carbonyl.

It is also possible to use mixtures of the stated metals with metal compounds and/or other additives, such as copper powder in combination with one of the aforementioned copper compounds; mixtures of copper powder with lithium halides, such as lithium chloride, or isocyanides, such as tert-butyl isocyanide; mixtures of iron powder with iron(III)chloride, optionally with the addition of carbon monoxide; mixtures of iron(III)chloride with benzoin; mixtures of iron(II)- or iron(III)chloride with trialkylphosphites; and mixtures of iron pentacarbonyl and iodine.

Preferred catalysts are iron(II)- and iron(III)salts and -complexes, particularly iron(II)- and iron(III)chloride, as well as iron powder; ruthenium(III)chloride, rithenium(II)dichloro-tris-triphenylphosphine, copper powder, copper bronze, copper(I)- and copper(II)salts and -complexes such as copper(I)chloride, copper(II)chloride, copper(I)bromide, copper(II)bromide; copper(II)acetate, copper(II)acetylacetonate, copper(II)benzoylacetonate, copper(II)sulfate, copper(II)nitrate, copper(I)cyanide and copper(I)iodide.

More especially preferred are copper powder, copper bronze, copper(I)- and copper(II)chloride or -bromide and copper(I)iodide, as well as mixtures thereof.

The catalysts are used generally in amounts of about 0.01 to 10 mol %, preferably 0.1 to 5 mol %, relative to the acrylonitrile.

The addition reaction of trichloroacetaldehyde with acrylonitrile is performed advantageously in the presence of an inert organic solvent. Suitable solvents are those in which the catalysts are sufficiently soluble, or which can form complexes with the catalysts, but which are inert to the trichloroacetaldehyde and the acrylonitrile. The following may be mentioned as examples of suitable solvents: alkanecarboxylic acid nitriles, particularly those having 2–5 carbon atoms, such as acetonitrile, propionitrile and butyronitrile; 3-alkoxypropionitriles having 1–2 carbon atoms in the alkoxy group, such as 3-methoxypropionitrile and 3-ethoxypropionitrile; aromatic nitriles, especially benzonitrile; aliphatic ketones preferably having a total of 3–8 carbon atoms, such as acetone, diethyl ketone, methylisopropyl ketone, diisopropyl ketone, methyl-tert-butyl ketone; alkyl and alkoxyalkyl esters of aliphatic monocarboxylic acids having a total of 2–6 carbon atoms, such as formic acid methyl and -ethyl esters, acetic acid methyl, -ethyl, -n-butyl, and -isobutyl esters, as well as 1-acetoxy-2-methoxyethane; cyclic ethers, such as tetrahydrofuran, tetrahydropyrane and dioxane; dialkyl ethers having 1–4 carbon atoms in each of the alkyl groups, such as diethyl ether, di-n-propyl ether and diisopropyl ether; N,N-dialkylamides of alkanecarboxylic acids having 1–3 carbon atoms in the alkyl group, such as N,N-dimethylformamide, N,N-dimethylacetamide; N,N-diethylacetamide and N,N-dimethylmethoxyacetamide; ethylene glycol and diethylene glycol dialkyl ethers having 1–4 carbon atoms in each of the alkyl groups, such as ethylene glycol dimethyl, -diethyl and -di-n-butyl ethers; diethylene glycol diethyl and -di-n-butyl ethers; and phosphorus acid-tris-N,N-dimethylamide (hexametapol). It is also possible to use excess acrylonitrile as solvent.

Preferred solvents for the addition reaction of trichloroacetaldehyde with acrylonitrile are alkanecarboxylic acid nitriles having 2–5 carbon atoms and 3-alkoxypropionitriles having 1–2 carbon atoms in the alkoxy group, particularly acetonitrile, butyronitrile, acrylonitrile and 3-methoxypropionitrile.

The 2,4,4-trichloro-4-formylbutyronitrile obtainable by the addition reaction of trichloroacetaldehyde with acrylonitrile is a novel compound and is likewise subject matter of the present invention.

The cyclisation of 2,4,4-trichloro-4-formylbutyronitrile can be performed in an open or closed system at temperatures between about 0° and 220° C., especially between about 80° and 200° C. Cyclisation is preferably performed in an open system. In the case of cyclisation in an open system, it is advantageous to perform it in the presence of hydrogen chloride, or in the presence of substances which form hydrogen chloride under the reaction conditions, such as phosgene, boron trichloride, aluminium chloride, trialkylammonium chlorides having 1–4 carbon atoms in each of the alkyl groups, phosphorus pentachloride, phosphorus oxychloride or phosphorus trichloride.

Cyclisation is performed preferably in the presence of hydrogen bromide and particularly hydrogen chloride.

The cyclisation reaction can be performed without adding a solvent; in the liquid phase or in the gaseous phase by merely heating the 2,4,4-trichloro-4-formylbutyronitrile; or in the presence of an organic solvent. Suitable organic solvents are for example: chlorinated aliphatic hydrocarbons, such as chloroform, methylene chloride and tetrachloroethane; optionally chlorinated aromatic hydrocarbons, such as benzene, toluene, xylenes and chlorobenzenes; N,N-dialkylamides of alkanecarboxylic acids having 1–3 carbon atoms, such as N,N-dimethylformamide, N,N-dimethylacetamide, N,N-diethylacetamide and N,N-dimethylmethoxyacetamide; cyclic amides, such as N-methyl-2-pyrrolidone, N-acetyl-2-pyrrolidone and N-methyl-γ-caprolactam; amides of carbonic acid, such as tetramethylurea and dimorpholinocarbonyl; amides of phosphorous acid, of phosphoric acid, of phenylphosphonic acid or of alkylphosphonic acids having 1–3 carbon atoms in the alkyl group, such as phosphoric acid triamide, phosphoric acid-tris-(N,N-dimethylamide), phosphoric acid trimorpholide, phosphoric acid tripyrrolinide, phosphoric acid-tris-(N,N-dimethylamide), methanephosphonic acid-bis-(N,N-dimethylamide); amides of sulfuric acid or of aliphatic or aromatic sulfonic acids, such as tetramethylsulfamide, methanesulfonic acid dimethylamide, or p-toluenesulfonic acid amide; aliphatic ketones, cyclic ethers, dialkyl ethers ethers as well as ethylene glycol and diethylene glycol dialkyl ethers of the aforementioned type, and also phosphorus trichloride and phosphorus oxychloride.

Preferred solvents for the cyclisation reaction are chloroform, methylene chloride, cyclic ethers and dialkyl ether having 1–4 carbon atoms in each of the alkyl groups, particularly dioxane and diethyl ether, as well as N,N-dialkylamides of lower aliphatic carboxylic acids, especially N,N-dimethylformamide.

The process according to the invention can be performed by firstly isolating the 2,4,4-trichloro-4-formylbutyronitrile formed by reacting trichloroacetaldehyde with acrylonitrile, and subsequently cyclising the 2,4,4-trichloro-4-formylbutyronitrile in a second stage of the process. The individual stages of this process are carried out as described in the foregoing.

An advantageous embodiment of the process according to the invention comprises reacting trichloroacetaldehyde with acrylonitrile at a temperature of 70°–140° C., in an inert solvent, and in the presence of 0.1–5 mol % of copper powder, copper bronze, copper(I)- or copper(II)chloride or -bromide or copper(I)iodide, or in the presence of a mixture of these substances, in a closed system; and then cyclising the 2,4,4-trichloro-4-formylbutyronitrile obtained after separation of the solvent, at a temperature of between 80° and 200° C. in a closed system, in the presence of hydrogen chloride, or of a substance forming hydrogen chloride under the reaction conditions, to obtain 2,3,5-trichloropyridine.

It is however possible to dispense with the isolation of 2,4,4-trichloro-4-formylbutyronitrile, and to perform the addition and cyclisation reactions in one operation. In this case, the reaction of trichloroacetaldehyde and acrylonitrile to 2,3,5-trichloropyridine is carried out at a temperature of between about 70° and 220° C., especially between about 130° and 200° C. This reaction can be performed either in an open system or in a closed system. If an open system is employed, it can be advantageous to perform the reaction in the presence of hydrogen chloride, or in the presence of substances which form hydrogen chloride under reaction conditions. Substances of this type are for example phosgene, boron trichloride, aluminium chloride, trialkylammonium chlorides having 1–4 carbon atoms in the alkyl groups, phosphorus pentachloride, phosphorus oxychloride or phosphorus trichloride. The single-stage production of 2,3,5-trichloropyridine is effected preferably in a closed system under a pressure corresponding to the respective reaction temperature, which pressure can be for example, depending on the reaction temperature, in the range of 1–50 bars. The production of 2,3,5-trichloropyridine in a closed system at a pressure of 1–30 bars is particularly preferred.

Preferred solvents for carrying out the process in a single stage are alkanecarboxylic acid nitriles having 2–5 carbon atoms and 3-alkoxypropionitriles having 1–2 carbon atoms in the alkyl group. Particularly suitable solvents are acetonitrile, butyronitrile and 3-methoxypropionitrile. After completion of the reaction, 2,3,5-trichloropyridine can be isolated in the customary manner, for example by evaporating off the solvent and purifying the crude product by means of steam distillation.

According to a further advantageous embodiment of the process according to the invention, trichloroacetaldehyde and acrylonitrile are reacted in acetonitrile, butyronitrile or 3-methoxypropionitrile as the solvent, in the presence of 0.1–5 mol % of copper powder, copper bronze, copper(I)- and copper(II)chloride or -bromide or copper(I)iodide, or of a mixture of these substances, at 130°–200° C. in a closed system under a pressure corresponding to the respective reaction temperature applied, directly to 2,3,5-trichloropyridine.

It becomes possible with the process according to the invention to produce 2,3,5-trichloropyridine in a very simple, economical and ecologically favourable manner, in good yields and with the use of cheap readily available starting materials. It is surprising that with the use of the starting materials according to the invention, there is obtained an addition product which, in contrast to prior known structurally similar addition products, can be readily cyclised, by displacement of a chlorine atom, to give 2,3,5-trichloropyridine. There is thus obtained, by use of a starting product (trichloroacetaldehyde) in which all chlorine atoms are bound to the same carbon atom, an end product in which the three chlorine atoms are located on different carbon atoms and in the desired positions. By virtue of this completely unexpected reaction, it is possible to dispense with the use of chlorinating agents and of further auxiliary reagents.

2,3,5-Trichloropyridine can be used, in a manner known per se, to produce various active substances, particularly herbicides (see for example U.S. Pat. Nos. 3,814,774, 3,894,862 and 4,046,553).

The process according to the invention is further illustrated by the following Examples.

EXAMPLE 1

(a) Production of 2,4,4-trichloro-4-formylbutyronitrile 22.0 g of trichloroacetaldehyde, 5.3 g of acrylonitrile and 0.5 g of copper(I)chloride with 30 ml of acetonitrile are heated in an enamel autoclave for 20 hours at 115° C. After cooling, the solvent is distilled off in a water-jet vacuum at about 40°–50° C.; there is then added to the residue 50 ml of diethyl ether, and the copper(I)-chloride which has precipitated is filtered off. After the diethyl ether has been distilled off, the residue is rectified under high vacuum, and the fraction boiling at 64°–65° C. and 400 Pa is collected. The yield is 13.6 g (60% of theory) of 2,4,4-trichloro-4-formylbutyronitrile in the form of a colourless oil.

IR spectrum (CHCl$_3$) in cm$^{-1}$: 2250 (CN), 1750(CO).

$^1$H-NMR spectrum (60 MHz in CDCl$_3$) in ppm: 9.15 (s, 1H, —CHO); 4.85 (t, 1H, H at C-2); 3.1 (d, 2H, 2H at C-3).

Elementary analysis for C$_5$H$_4$Cl$_3$NO (molecular weight 200.45): calculated: C 29.96% H 2.01% N 6.99% Cl 53.06%. found: C 29.89% H 2.13% N 6.95% Cl 52.67%.

(b) Production of 2,3,5-trichloropyridine 13.6 g of 2,4,4-trichloro-4-formylbutyronitrile obtained according to (a), with the addition of 1.0 g of AlCl$_3$, is heated in an enamel autoclave for 1 hour at 60° C. The dark crude product is afterwards distilled with steam, in the process of which the 2,3,5-trichloropyridine precipitates, in the distillate, in the form of white crystals. The yield is 9.1 g (83% of theory) of 2,3,5-trichloropyridine, m.p. 49°–50° C.

EXAMPLE 2

(a) 14.7 g of trichloroacetaldehyde, 5.3 g of acrylonitrile and 0.5 g of copper(I)chloride in 40 ml of 3-methoxypropionitrile are heated at 80° to 85° C. In the course of the reaction, the boiling point of the mixture rises and after about 30 hours reaches 125°–130° C. After cooling, the dark contents of the flask are extracted with diethyl ether. The diethyl ether is distilled off, and the brown oil remaining is heated to 100° C. (bath temperature) in a water-jet vacuum, whereupon 3-methoxypropionitrile distills off. The residue is rectified under high vacuum. The yield is 10.2 g (51% of theory) of a colourless oil, which is identical to the product obtained according to Example 1(a).

(b) The 2,4,4-trichloro-4-formyl-butyronitrile obtained according to the above section a) is converted, by three hours' heating at 130° C. and subsequent steam distillation, into 2,3,5-trichloropyridine (yield 80% of theory.

EXAMPLE 3

20 g of 2,4,4-trichloro-4-formyl-butyronitrile produced according to Example 1(a) is dissolved in 20 ml of diethyl ether, and the solution is treated at 20°–25° C. for 5 hours with a stream of hydrogen bromide gas. The diethyl ether is subsequently distilled off in vacuo, and the residue is purified by steam distillation to obtain 13.6 g (60% of theory) of 2-bromo-3,5-dichloropyridine in the form of white crystals, m.p. 42° C.

A similarly good result is obtained by using, in place of diethyl ether, chloroform as the solvent, the procedure otherwise being the same.

EXAMPLE 4

(a) Production of 2,4,4-trichloro-4-formylbutyronitrile 14.7 g of trichloroacetaldehyde, 13.2 g of acrylonitrile and 0.63 g of copper powder (activated using the process given in Org. Synth., Coll. Vol.III, 339 for copper bronze) are heated in a pressure reaction vessel at 105° C. for 12 hours. The excess acrylonitrile is subsequently distilled off at 40°–50° C. in a water-jet vacuum.

There is obtained as residue 18.2 g of a dark oil which, according to gas-chromatographical analysis, consists to the extent of 85.4% of 2,4,4-trichloro-4-formylbutyronitrile, which corresponds to a yield of 77% of theory.

(b) Production of 2,3,5-trichloropyridine 2,4,4-Trichloro-4-formylbutyronitrile (18.2 g), obtained under (a), is introduced dropwise within 15 minutes into a vertical jacket tube which is 40 cm long and 2.5 cm wide and which is half filled with Raschig rings, the jacket of the tube being heated with hot oil at 175°–180° C. There is simultaneously fed in from below, against the reaction mixture, a weak flow of hydrogen chloride. The dark resin dripping from the reaction vessel is distilled with steam. The yield is 11.5 g (85% of theory) of 2,3,5-trichloropyridine in the form of white crystals, m.p. 49°–50° C.

EXAMPLE 5

(a) Production of 2,4,4-trichloro-4-formylbutyronitrile

A mixture of 14.7 g of trichloroacetaldehyde, 13.2 g of acrylonitrile and 0.63 g of copper bronze (activated by the process given in Org. Synth., Coll. Vol. III, 339) is refluxed for 48 hours. The excess acrylonitrile is subsequently distilled off at 40°–50° C. in a water-jet vacuum. There is obtained as residue 17.3 g of a dark oil which, according to gas-chromatographical analysis, consists to the extent of 88.5% of 2,4,4-trichloro-4-formylbutyronitrile, which corresponds to a yield of 76.5% of theory.

(b) Production of 2,3,5-trichloropyridine

The 2,4,4-trichloro-4-formyl-butyronitrile (17.3 g) obtained according to (a) is heated, as a weak stream of hydrogen chloride is being introduced, at 80°–85° C. for 24 hours. The entire reaction mixture is subsequently distilled with steam. The yield is 10.0 g (72% of theory) of 2,3,5-trichloropyridine in the form of white crystals, m.p. 49°–50° C.

EXAMPLE 6

Production of 2,3,5-trichloropyridine

Hydrogen chloride is passed into a solution of 25.0 g (0.125 mol) of 2,4,4-trichloro-4-formylbutyronitrile in 50 mml of N,N-dimethylformamide at a rate such that the temperature of the reaction mixture does not exceed 120° C. After completion of the reaction, the reaction mixture is poured into ice water. The beige-coloured precipitate is filtered off and dried. There is obtained 15.1 g (66% of theory) of 2,3,5-trichloropyridine, m.p. 48°–50° C.

EXAMPLE 7

Production of 2,3,5-trichloropyridine 10.3 g of phosphorus pentachloride is added portionwise at a maximum of 60° C. to 40.0 g of dimethylformamide. The solution obtained is subsequently saturated with hydrogen chloride, whereupon the temperature rises to 95° C. After cooling to 50° C. there is added dropwise 20.0 g of 2,4,4-trichloro-4-formylbutyronitrile (produced according to Example 1(a) in such a manner that the temperature of 75° C. is not exceeded. After completion of the addition of 2,4,4-trichloro-4-formylbutyronitrile, the mixture is heated at 100° C. for 1 hour. The reaction mixture at 60° C. is subsequently poured onto ice, whereupon 2,3,5-trichloropyridine precipitates in solid form. After filtration and drying, the yield is 16.2 g (89% of theory) of 2,3,5-trichloropyridine, m.p. 49°–51° C.

EXAMPLE 8

17.7 g of trichloroacetaldehyde, 5.3 g of acrylonitrile and 0.5 g of copper(I)chloride with 40 ml of acetonitrile are heated in an enamel autoclave for 1 hour at 180° C. The reaction mixture is cooled; the solvent is subsequently distilled off at about 40°–50° C. in a water-jet vacuum, the residue is subjected to steam distillation, and 2,3,5-trichloropyridine precipitates in the distillate in the form of white crystals, m.p. 49°–50° C.; yield=11.1 g (61% theory).

2,3,5-Trichloropyridine is obtained in similarly good yield by using, in place of copper(I)chloride, 0.5 g of copper bronze (produced according to Organic Syntheses, Coll. Vol.III, 339), or 0.5 g of anhydrous iron(II)chloride, the procedure being otherwise as described above.

EXAMPLE 9

17.7 g of trichloroacetaldehyde, 5.3 g of acrylonitrile, 0.3 g of ruthenium(II)dichloro-tris-triphenylphosphine [T. A. Stephenson and G. Wilkinson, Inorg. Nucl. Chem., 28, 945 (1966)] and 30 ml of 3-methoxypropionitrile are heated for 2 hours at 170° C. in an enamel autoclave. After processing in a manner analogous to that described in Example 1, the yield is 10.5 g (58% of theory) of 2,3,5-trichloropyridine.

2,3,5-Trichloropyridine is obtained in likewise good yield by replacing in the above example the 3-methoxypropionitrile by butyronitrile.

EXAMPLE 10

17.7 g of trichloroacetaldehyde, 5.3 g of acrylonitrile and 0.5 g of copper(I)chloride with 40 ml of acetonitrile are heated for ½ hour at 190° C. in an enamel autoclave. After cooling the mixture, the solvent is distilled off at about 40°–50° C. in a water-jet vacuum. The residue is subjected to steam distillation, and in the distillate 2,3,5-trichloropyridine precipitates out in the form of white crystals, m.p. 49°–50° C.; yield=11.3 g (62% of theory).

2,3,5-Trichloropyridine is obtained in similarly high yield when the reaction temperature is held for 2 hours at 170° C. or for 6 hours at 150° C., using otherwise the same procedure.

What is claimed is:

1. A process for producing 2,3,5-trichloropyridine, which process comprises causing trichloroacetaldehyde to undergo an addition reaction, in the presence of a catalyst, with acrylonitrile, and cyclising the formed 2,4,4-trichloro-4-formylbutyronitrile of the formula I

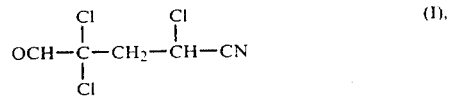

with the splitting-off of water, to give 2,3,5-trichloropyridine.

2. A process according to claim 1, wherein the addition reaction of trichloroacetaldehyde with acrylonitrile is performed at a temperature of 70°–140° C.

3. A process according to claim 1, wherein the addition reaction of trichloroacetaldehyde with acrylonitrile is performed in a closed system at a temperature of 70°-140° C. and at a pressure corresponding to the applied reaction temperature.

4. A process according to claim 1, wherein there is used as catalyst for the addition reaction of trichloroacetaldehyde with acrylonitrile a metal of the main group VIII or of the subgroups VIa, VIIa, Ib and IIb, an oxide of a metal of this type, a salt of a metal of this type or a complex compound of a metal of this type.

5. A process according to claim 1, wherein the catalyst used for the addition reaction of trichloroacetaldehyde with acrylonitrile is selected from the group consisting of: iron(II)- and iron(III)salts or complexes thereof, iron powder, ruthenium(III)chloride, ruthenium(II)dichloro-tris-triphenylphosphine, copper powder, copper bronze, copper(I)- or copper(II)salts or complexes thereof.

6. A process according to claims 1 or 5, wherein the catalyst used for the addition reaction of trichloroacetaldehyde with acrylonitrile is selected from the group consisting of: copper powder, copper bronze, copper-(I)- or copper(II)chloride or -bromide, copper(I)iodide, or mixtures thereof.

7. A process according to claim 1 or 4-6, wherein the catalyst for the addition reaction of trichloroacetaldehyde with acrylonitrile is used in amounts of about 0.01 to 10 mol %, preferably 0.1-5 mol %, relative to the acrylonitrile.

8. A process according to claim 1, wherein the addition reaction of trichloroacetaldehyde with acrylonitrile is performed in the presence of an inert organic solvent.

9. A process according to claims 1 or 8, wherein the addition reaction of trichloroacetaldehyde with acrylonitrile is performed in an alkanecarboxylic acid nitrile having 2-5 carbon atoms, in a 3-alkoxypropionitrile having 1-2 carbon atoms in the alkyl group, or in excess acrylonitrile, as the solvent.

10. A process according to claim 1, wherein cyclisation of the 2,4,4-trichloro-4-formylbutyronitrile formed by the addition reaction of trichloroacetaldehyde with acrylonitrile is performed at a temperature of between 0° and 220° C., preferably between about 80° and 200° C.

11. A process according to claim 1, wherein the cyclisation reaction is performed at a temperature of between 80° and 200° C. in an open system, and in the presence of hydrogen chloride, or in the presence of substances which form hydrogen chloride under the reaction conditions.

12. A process according to claims 1 or 11, wherein cyclisation of 2,4,4-trichloro-4-butyronitrile is performed in the presence of hydrogen bromide, and particularly in the presence of hydrogen chloride.

13. A process according to claim 1, wherein cyclisation of 2,4,4-trichloro-4-formylbutyronitrile is performed, in the absence of a solvent, by heating in the liquid or in the gaseous phase.

14. A process according to claim 1, wherein cyclisation of 2,4,4-trichloro-4-formylbutyronitrile is performed in the presence of an organic solvent.

15. A process according to claims 1 or 14, wherein cyclisation of 2,4,4-trichloro-4-formylbutyronitrile is performed in the presence of chloroform, methylene chloride, cyclic ethers, dialkyl ethers having 1-4 carbon atoms in each of the alkyl groups, or N,N-dialkylamides of lower aliphatic carboxylic acids.

16. A process according to claim 1, wherein the 2,2,4-trichloro-4-formylbutyronitrile formed by the addition reaction of trichloroacetaldehyde with acrylonitrile is firstly isolated, and is subsequently cyclised in a second stage of the process.

17. A process according to claims 1 or 16, wherein trichloroacetaldehyde is reacted with acrylonitrile at a temperature of 70°-140° C. in an inert solvent, in the presence of 0.1-5 mol % of copper powder, copper bronze, copper(I)- and copper(II)chloride or -bromide or copper(I)iodide, or in the presence of a mixture of these substances, in a closed system; and the 2,2,4-trichloro-4-formylbutyronitrile obtained after removal of the catalyst and solvent is cyclised at a temperature of between 80° and 200° C. in an open system, in the presence of hydrogen chloride or in the presence of a substance which forms hydrogen chloride under the reaction conditions, to give 2,3,5-trichloropyridine.

18. A process according to claim 1, wherein trichloroacetaldehyde and acrylonitrile are reacted at a temperature of between 70° and 220° C. in the presence of a catalyst, without isolation of the intermediately formed 2,2,4-trichloro-4-formylbutyronitrile, directly to 2,3,5-trichloropyridine.

19. A process according to claims 1 or 18, wherein the reaction of trichloroacetaldehyde and acrylonitrile is performed in a closed system at a pressure corresponding to the respective reaction temperature applied.

20. A process according to claims 1, 18 or 19, wherein the reaction of trichloroacetaldehyde and acrylonitrile is performed in the presence of an alkanecarboxylic acid nitrile having 2-5 carbon atoms or of a 3-alkoxypropionitrile having 1-2 carbon atoms in the alkyl group, as the solvent.

21. A process according to claims 1 or 18-20, wherein trichloroacetaldehyde and acrylonitrile are reacted in acetonitrile, butyronitrile or 3-methoxypropionitrile, as the solvent, in the presence of 0.1-5 mol % of copper powder, copper bronze, copper(I)- or copper(II)chloride or -bromide or copper(I)iodide, or in the presence of a mixture of these substances, at 130° to 200° C., in a closed system at a pressure corresponding to the particular reaction temperature applied, directly to 2,3,5-trichloropyridine.

22. 2,4,4-Trichloro-4-formylbutyronitrile.

23. A process for producing 2,4,4-trichloro-4-formylbutyronitrile, wherein trichloroacetaldehyde is caused to undergo, in the presence of a catalyst, an addition reaction with acrylonitrile.

24. A process according to claim 23, wherein the addition reaction of trichloroacetaldehyde with acrylonitrile is performed in the presence of an organic solvent at a temperature of 70° to 140° C.

25. A process according to claims 23 or 24, wherein the addition reaction of trichloroacetaldehyde with acrylonitrile is performed in the presence of excess acrylonitrile as the solvent.

26. A process according to claim 23, wherein the addition reaction of trichloroacetaldehyde with acrylonitrile is performed in the presence of a metal of the main group VIII or of the subgroups VIa, VIIa, Ib or IIb of the periodic system, of an oxide or of a salt of a metal of this type, as the catalyst.

27. A process according to claims 23 or 26, wherein the catalyst used for the addition reaction of trichloroacetaldehyde with acrylonitrile is: iron(II)chloride, iron(III)chloride, iron powder, ruthenium(III)chloride, ruthenium(II)dichloro-tris-triphenylphosphine, copper powder, copper bronze, copper(I)chloride, copper(II)- chloride, copper(I)bromide, copper(II)bromide, copper(II)acetate, copper(II)acetylacetonate, copper(II)benzylacetonate, copper(II)sulfate, copper(II)nitrate, copper(I)cyanide or copper(I)iodide.

28. A process according to claims 23 or 26, wherein the catalyst used for the addition reaction of trichloroacetaldehyde with acrylonitrile is: copper powder, copper bronze, copper(I)chloride, copper(II)chloride, copper(I)bromide, copper(II)bromide or copper(I)iodide, or a mixture thereof.

29. A process according to claims 23 or 26-28, wherein the catalyst for the addition reaction of trichloroacetaldehyde with acrylonitrile is used in amounts of 0.01 to 10 mol %, preferably 0.1-5 mol %, relative to the acrylonitrile.

* * * * *